United States Patent [19]

Falk

[11] Patent Number: 4,806,018

[45] Date of Patent: Feb. 21, 1989

[54] ANGULAR REFLECTANCE SENSOR

[75] Inventor: Robert A. Falk, Renton, Wash.

[73] Assignee: The Boeing Company, Seattle, Wash.

[21] Appl. No.: 69,637

[22] Filed: Jul. 6, 1987

[51] Int. Cl.[4] ...................... G01N 21/47; G01B 11/30
[52] U.S. Cl. .................................... 356/446; 250/227; 356/371
[58] Field of Search ............... 356/446, 340, 342, 343, 356/371; 250/227

[56] References Cited

U.S. PATENT DOCUMENTS

| | | | |
|---|---|---|---|
| 3,984,189 | 10/1976 | Seki et al. | 356/446 |
| 4,092,068 | 5/1978 | Lucas et al. | 356/446 |
| 4,111,524 | 9/1978 | Tomlinson, III | 350/96.19 |
| 4,208,094 | 6/1980 | Tomlinson, III et al. | 350/96.20 |
| 4,213,708 | 7/1980 | Lucas | 356/446 |
| 4,239,330 | 12/1980 | Ashkin et al. | 350/96.18 |
| 4,412,746 | 11/1983 | Yokouchi | 356/446 |
| 4,474,424 | 10/1984 | Wagner | 350/96.15 |
| 4,479,717 | 10/1984 | Cornillault | 250/227 X |
| 4,554,449 | 11/1985 | Taniuchi et al. | 250/227 |

OTHER PUBLICATIONS

Hsia et al., "Bidirectional Reflectometry. Part I," Journal of Research of the National Bureau of Standards, vol. 80(A), No. 2, Mar.-Apr. 1976, pp. 189-205.
Richmond et al., "Bidirectional Reflectometry. Part II," Journal of Research of the National Bureau of Standards, vol. 80(A), No. 2, Mar.-Apr. 1976, pp. 207-220.
Brodmann et al., "Optical Roughness Measuring Instrument for Fine-Machined Surfaces", Optical Engineering/May/Jun. 1985, vol. 24 #3, pp. 408-413.

*Primary Examiner*—Vincent P. McGraw
*Attorney, Agent, or Firm*—Christensen, O'Connor, Johnson & Kindness

[57] ABSTRACT

An angular reflectance sensor having no moving parts and capable of the essentially simultaneous measurement of the reflectivity of a surface at a plurality of angles. The sensor comprises a quarter pitch graded index lens (78) having first end face (82) and second end face (84) and an optical axis (86). Light is coupled from an optical source (72) to an input position (88) on the first end face. A plurality of detectors are provided, each detector having associated therewith an output position (97-99) on the first end face. Each detector comprises a photodetector (74-76) and a fiber optic cable (94-96) for coupling light from the associated output position to the photodetector. The second end face of the lens is positioned adjacent a surface. Light reflected from the surface at a particular angle is focused by the lens to a particular output position, and thus to a particular photodetector.

8 Claims, 1 Drawing Sheet

ANGULAR REFLECTANCE SENSOR

FIELD OF THE INVENTION

The present invention relates to a sensor for measuring the reflectance of a surface as a function of the reflection angle.

BACKGROUND OF THE INVENTION

There are a number of applications in which the measurement of the angular reflectance properties or the bidirectional reflectance distribution function (BRDF) of a material is important. These applications include materials characterization, tactile sensors for robotics, and fluid/aerosol particle size evaluation. One material characterization application involves the measurement of paint gloss. Conventional techniques for paint gloss measurement utilize optical sensors mounted on arms, such that the angle viewed by the sensor with respect to the surface can be changed. Such designs suffer from the fact they are not compact, and involve moving parts. Another material characterization application is the determination of the finish or the smoothness of a surface. For a machined part, the surface smoothness may be particularly important if the part is to be used in a press-fit joint. Typically, surface testing of this type is done by carrying out a visual comparison of the part to be tested with a series of standard samples.

In the robotics field, surface roughness measurements can provide significant benefits in tactile sensing. For example, it is known that a person estimates the force needed to hold an object by visually estimating the surface roughness of the object to be held. Thus an angular reflectance sensor that was sufficiently compact to mount within a robot finger could provide a surface roughness measurement to a robotics system, thereby permitting the robotics system to estimate the force required to hold an object. Such measurements could also of course be used to aid in identifying the object.

It is well known that the catastrophic failure of an engine, such as an aircraft engine, is usually preceded by a sharp rise in the particulate matter suspended in the engine oil in the 15-30 minutes before failure. It is also known that the size of particles suspended in oil determines the angular reflectance characteristics of the suspension. For example, large particles tend to produce retroreflection, whereas small particles tend to produce uniform angular scattering. Thus an effective sensor for measuring the angular reflectance of a suspension could find ready application in monitoring of engine oil for contaminants.

SUMMARY OF THE INVENTION

The present invention provides an angular reflectance sensor that is capable of essentially simultaneous measurement of the reflectance of a surface at a plurality of angles. In a preferred embodiment, the sensor is extremely compact and simple in construction as compared to prior angular reflectance sensor.

In the preferred embodiment, the angular reflectance sensor comprises a quarter pitch graded index lens having first and second end faces and an optical axis. Light is coupled from an optical source to an input position on the first end face of the graded index lens. A plurality of detectors is provided, each detector having associated therewith an output position on the first end face. Each detector comprises a photodetector and means for optically coupling light from its associated output position to the photodector. Thus, when the second end face of the graded index lens is positioned adjacent the surface, the light coupled to each photodetector is a measure of the reflectance of the surface at a particular angle. The angle is a function of the distance between the output position associated with the photodetector and the optical axis of the graded index lens. An embodiment comprising a conventional converging lens is also described, in which an optical source and a plurality of photodetectors are positioned on one side of the lens at focal distance f therefrom.

DETAILED DESCRIPTION OF THE INVENTION

Figure 1:
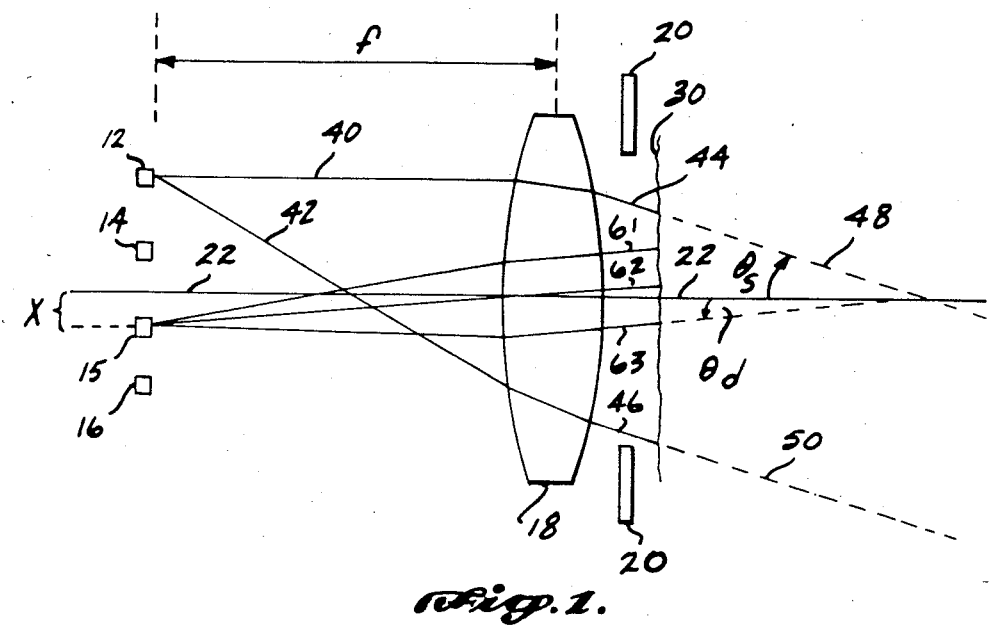
FIG. 1 is a diagram showing the angular reflectance sensor of the present invention using a lens.

Although the preferred embodiment of the present invention is implemented using a graded index lens and fiber optic cables, the concept behind the present invention can be most readily understood with reference to the embodiment shown in FIG. 1 in which a conventional converging lens is used. The system shown in FIG. 1 comprises optical source 12, a plurality of photodetectors 14-16, lens 18 and aperture forming device 20. In an actual embodiment, more than three photodetectors would typically be used. Lens 18 has an optical axis 22 and a focal length f. Source 12 and photodetectors 14-16 are positioned at distance f from the lens on a first side of the lens (the left side in FIG. 1). Aperture forming device 20 is positioned on the opposite side of the lens from the source and photodetectors, and the entire device is positioned adjacent a surface 30 whose angular reflectance characteristic is to be measured.

Because source 12 is positioned at the focal distance f from lens 18, light emitted by source 12, symbolized by rays 40 and 42, is converted by the lens into a collimated beam, symbolized by rays 44 and 46 and phantom lines 48 and 50. Thus all light from source 12 strikes surface 30 at a common angle $\phi_s$. Light reflected by surface 30 is processed by lens 18 in a similar manner. In particular, all light reflected from surface 30 at a given angle will be focused by the lens to a particular point at the focal distance f from the lens. In FIG. 1, light reflected from surface 30 at an angle $\phi_d$ is symbolized by rays 61-63, and lens 18 focuses all such rays onto a single photodetector 15. The angle $\phi_d$ and the distance x between photodetector 15 and optical axis 22 of lens 18 is given by $$x = f \cdot \tan \phi_d \qquad (1)$$

As a result, each photodetector 14-16 responds to the light reflected from surface 30 at a particular reflectance angel $\phi_d$. Measurement of the light output by the photodetectors thus provides a direct measure of the angular reflectance characteristic of the surface.

Figure 2:
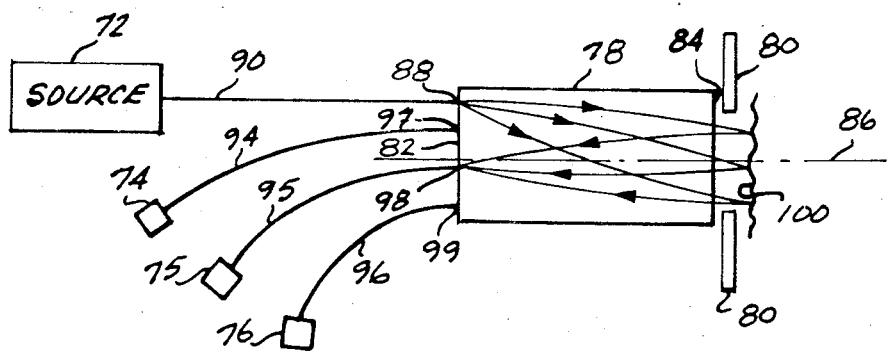
FIG. 2 is a diagram showing the angular reflectance sensor of the present invention using a graded index lens and fiber optics.

A second and preferred embodiment of the present invention is shown in FIG. 2. This embodiment includes optical source 72, a plurality of photodetectors 74-76, quarter pitch GRIN lens 78 and aperture-forming device 80. GRIN lens 78 has a cylindrical shape, and includes opposed faces 82 and 84 and optical axis 86.

Source 72 is coupled to face 82 by fiberoptic cable 90, and photodetectors 74–76 are coupled to face 82 by fiberoptic cables 94–96, respectively. Fiber optic cable 90 contacts face 82 at input position 88, and fiber optic cables 94–96 contact face 82 at output positions 97–99, respectively. Aperture-forming device 80 is positioned adjacent face 84. In use, the sensor is positioned such that face 84 is positioned adjacent surface 100 whose angular reflectance characteristic is to be measured.

A quarter pitch GRIN lens has the property that its index of refraction n at a given point within the lens is a quadratic function of the distance of the point from optical axis 86, i.e., $$n(x) = n_0 - n_1 x^2 \qquad (2)$$

where x is the distance from optical axis 86. As a result, light entering face 82 of GRIN lens 78 at a particular distance x from the optical axis is refracted such that it strikes surface 100 at a single angle $\phi_s$ that is a function of the distance between the point of enry of the light at face 82 and optical axis 86. In a similar manner, all light leaving surface 100 at a particular angle $\phi_d$ is refracted by GRIN lens 78 to a particular point on face 82. As a result, the amount of light received by each photodetector 74–76 is a function of the position of the corresponding output positions, and in particular the distance from the output position to optical axis 86. Thus functionally, the embodiment of FIG. 2 operates in a manner similar to that of the embodiment of FIG. 1. However, unlike the embodiment of FIG. 1, the embodiment of FIG. 2 can be constructed such that source 72 and photodetectors 74–76 are remote from quarter pitch GRIN lens 78 and surface 100, thereby enabling a much more compact sensor to be fabricated. For example, a typical quarter pitch GRIN lens has a length of 10 mm and a diameter of 2-3 mm. From twenty to thirty fiber optic cables of 100 micron diameter can be abutted against face 82 of such a GRIN lens, to provide a compact and versatile angular reflectance sensor.

For many materials, the angular reflectance characteristic will be essentially independent of the angle at which light from the illumination source strikes the surface. For such materials, for both of the illustrated embodiments, source 12 could be placed at any position with respect to the optical axis. However, the position illustrated, at one edge of the lens, will in general be preferred because it provides the greatest range and the least redundancy in the information collected. For example, were the input position to be located on the optical axis, then the photodetectors having output positions on opposite sides of the input position would collect redundant information. Furthermore, locating the input position on the optical axis would make it impossible to precisely measure specular reflection in which $\phi_s$ is equal to $\phi_d$.

In a preferred embodiment, photodetectors 74–76 could comprise a photodetector array, together with conventional sampling circuitry so that all data could be collected over a very short time interval, i.e., essentially simultaneously. This feature illustrates the significant advantage of the present invention with respect to prior reflectance measuring devices in which the sensor is mounted to an arm that is oriented at various angles with respect to the surface. In the latter type of sensor, the arm must be continuously moved, and data collected serialy at the various sensor positions.

For measuring the reflectance of a surface that is not structured, photodetectors 74–76 may comprise a one-dimensional photodetector array, and output positions 97–99 could similraly be arranged in a one-dimensional line across face 82. For a structured surface in which the reflectance is a function of the orientation of the plane defined by the source and detector with respect to the surface, a two-dimensional photodetector array could advantageously be employed. Because of the significant number of detectors involved in a two-dimensional array, a CCD array would be preferred for such an embodiment. In general, the maximum off-axis angle that could be handled by the sensor shown in FIG. 2 would be the angle whose sine was equal to the numerical aperture of fiber optic cables 90 and 94–96. Since a typical upper limit for a numerical aperture of fiber optic cables is 0.3, a maximum off-axis angle of about 17°–18° can readily be achieved.

While the preferred embodiments of the invention have been illustrated and described, variations will be apparent to those skilled in the art. Accordingly, the invention is not to be limited to the specific embodiments described, and the true scope of the invention is to be determined by reference to the following claims.

the embodiments of the invention in which an exclusive property or privilege is claimed are defined as follows:

1. An angular reflectance sensor for measuring the reflectance of a surface as a function of reflection angle, the sensor comprising:
   a quarter pitch graded index lens having first and second end faces and an optical axis;
   an optical source and means for coupling light from the source to an input position on the first end face of the graded index lens; and
   a plurality of detectors, each detector having associated therewith an output position on the first end face of the graded index lens, each detector comprising a photodetector and means for optically coupling light from its associated output position to the photodetector, such that when the second end face of the graded index lens is positioned adjacent the surface, the light coupled to each photodetector is a measure of the reflectance of the surface at an angle that is a function of the distance between the output position associated with the photodetector and the optical axis of the graded index lens.

2. The sensor of claim 1, wherein each means for optically coupling light comprises a fiber optic cable.

3. The sensor of claim 1, wherein the output positions form a line on the first end face.

4. The sensor of claim 3, wherein the photodetectors comprise an integrated photodetector array.

5. The sensor of claim 1, wherein the output positions form a two-dimensional array on the first end face.

6. The sensor of claim 5, wherein the photodetectors comprise a two-dimensional photodetector array.

7. The sensor of claim 6, wherein the photodetector array comprises a CCD array.

8. An angular reflectance sensor for measuring the reflectance of a surface as a function of refection angle, the sensor comprising:
   a lens having a positive focal length f and an optical axis;
   an optical source positioned on a first side of the lens at a distance f therefrom; and
   a plurality of photodetectors positioned on the first side of the lens, each photodetector being at a distance f from the lens;
   whereby when the sensor is positioned such that the surface is adjacent a second side of the lens opposite the first side, each photodetector receives light from the source that has been reflected by the surface at a reflection angle that is a function of the distance of the photodetector from the optical axis.

* * * * *